(12) United States Patent
Luo et al.

(10) Patent No.: US 8,367,811 B2
(45) Date of Patent: Feb. 5, 2013

(54) RADIOACTIVE MATERIAL CONTAINING CHITOSAN FOR INHIBITING CANCER AND PREPARATION METHOD THEREOF

(75) Inventors: Tsai-Yueh Luo, Longtan Township, Taoyuan County (TW); I-Chung Tang, Pingjhen (TW); Jian-Wen Chen, Yongjing Township, Changhua County (TW); Kwei-Luen Hsu, Hsinchu (TW); Yu-Lung Wu, Bade (TW); Te-Sheng Liang, Taipei (TW); Chang-Mau Sheng, Taipei (TW); Jin-Jenn Lin, Longtan Township, Taoyuan County (TW); Ching-Jun Liou, Longtan Township, Taoyuan County (TW); Jyh-Daw Sheu, Bade (TW)

(73) Assignee: Atomic Energy Council-Institute of Nuclear Energy Research, Taoyuan (TW)

( * ) Notice: Subject to any disclaimer, the term of this patent is extended or adjusted under 35 U.S.C. 154(b) by 435 days.

(21) Appl. No.: 12/263,573

(22) Filed: Nov. 3, 2008

(65) Prior Publication Data

US 2010/0111860 A1     May 6, 2010

(51) Int. Cl.
*C07F 13/00*     (2006.01)

(52) U.S. Cl. ........ 534/14; 424/1.11; 424/1.65; 424/1.73
(58) Field of Classification Search ................. 424/1.11, 424/1.65, 1.69, 1.73, 9.1, 9.2; 534/7, 10–16; 549/200

See application file for complete search history.

(56) References Cited

PUBLICATIONS

Riddoch et al (Bioconjugate Chemistry, 2006, vol. 17, No. 1, pp. 226-235).*

* cited by examiner

*Primary Examiner* — D L Jones
(74) *Attorney, Agent, or Firm* — Sinorica, LLC; Ming Chow

(57) ABSTRACT

A radioactive material containing chitosan for inhibiting cancer and a preparation method thereof are revealed. The adioactive material containing chitosan is formed by using SOCTA chelating agent to connect chitosan and radionuclides such as $^{188}$Re, and Tc-99m etc. The preparation method of the radioactive material containing chitosan includes the steps of: prepare SOCTA-Chitosan compound; and prepare M(radionuclide)-SOCTA-Chitosan compound. By biocompatibility and clotting in alkaline environment of human blood of chitosan, the radioactive material containing chitosan is injected into cancer and staying there for a long time so as to achieve effectively treatment.

5 Claims, 6 Drawing Sheets

RADIOACTIVE MATERIAL CONTAINING CHITOSAN FOR INHIBITING CANCER AND PREPARATION METHOD THEREOF

BACKGROUND OF THE INVENTION

1. Field of Invention

The present invention relates to a radioactive material for inhibiting cancer and a preparation method thereof, especially to a radioactive material containing chitosan for inhibiting cancer and a preparation method thereof that are applied to fields of cancer cells and tumor inhibition.

2. Description of Related Art

According to statistics of Department of Health in 2006, most of leading causes of death in Taiwan relates to tumors and cancer has become the top leading cause of death for 25 years. For cancers, the main types of treatment include surgery, chemotherapy, and radiation therapy. Although surgery can remove tumors and tumor-like lesions, it has restricted applications in tumor metastasis and hematological malignancy. As to the chemotherapy, it uses chemical substances as drugs to treat disease. Patients require different treatment planning according to their physical strength, tumor size and stages. The chemotherapy can be applied alone, before the surgery, or in combinations with the radiation therapy. Yet it has toxicity for human tissue cells and severe side effects. Due to stereotactic location and progress of computer software, the radiation therapy gives good local control of the tumors and further increases the cure rate. But it such treatment still has acute or chronic side effects such as fatigue, infection, anemia, decreased appetite and dehydration etc. By drug specificity in uncontrolled cell division of tumor cells, the chemotherapy blocks progression in cell growth phase so that tumor cell division and proliferation are inhibited and the tumor cell apoptosis is enhanced. However, such kind of drug response affects all rapidly dividing cells in general. Not only tumor cells, the drugs also kill normal cells that divide quickly such as hair follicle cells, gastrointestinal lining and hematopoietic cells in bone marrow so that is has cytotoxic effect. Along with quick development of tumor molecular biology and genomic medicine, cancer diagnosis and treatment have a lot of new discoveries. Thus the most important issue in cancer therapy is how to blocks growth and proliferation of tumor cells directly without affecting normal cells.

The applications of external materials in medical use is firstly seen in hard tissue repair. The official record in medical literature starts from the middle of 16 century. Some people use iron wire for repairing fracture, silver wire for fixing fragments in long bone fracture, and metallic plate for fracture repair. After 1988, a new technology—human tissue engineering is provided. According to principles of cell biology and engineering, tissues cells in vivo are separated to be cultured and proliferated in vitro and then are implanted into scaffolds made from degradable biomedical materials. The scaffold is implanted into damaged tissues or organs. Along with cell secretion of matrix and degradation of biomedical material, a new tissue or organ with original morphology functions is formed. Thus the purposes of tissue repair and function reconstruction are achieved. In accordance with the material being used, biomedical material includes polymer (both artificial and natural), metals, ceramics and composite materials. The polymer materials are generally applied to surface devices, external communicating devices, and implant devices. The biocompatibility assessment of the biomedical materials such as such as cytotoxicity tests, sensitization tests, intracutaneous reactivity tests, systemic toxicity, tests for genotoxicity, hemolysis, carcinogenicity, reproductive toxicity, and biodegradability are required, based on type and duration of contact. A good biomedical material has the following features: (1) medical functions (2) biocompatibility (3) biological stability (4) market competitiveness.

The natural polymer that is degraded by enzymes in bodies shows quite good biocompatibility and includes fibrin, collagen, gelatin, hyaluronic acid, chitosan, and alginate extracted from plants. Chitosan is produced by deacetylation of chitin with high-concentrated hot alkali so that the acetyl group in chitin is removed and turned into the amino group. Chitosan is a linear polysaccharide composed of randomly distributed β-(1-4)-linked D-glucosamine (deacetylated unit) and N-acetyl-D-glucosamine (acetylated unit) and chemical formula of chitosan is shown in FIG. 1. Chitosan is positively charged and soluble in acidic solution (pH<6.5). Due to high-reactive amino group, chitosan is often converted into derivatives. Chitosan will not induce allergic reaction and rejection so it has good biocompatibility with tissues. After being degraded by enzymes, nontoxic aminosaccharides are generated and are absorbed without side effects. Moreover, chitosan is featured on antimicrobial activity and removal of toxic metal, broadly applied to medical filed. Thus chitosan, as natural polymer, has received much attention recently. It can be produced into micron/nano-scale particles used as carriers for drugs or applied to wound dressing material, artificial livers, bone and joint repair, nerve repair, and antimicrobial material.

There is no tumor inhibitor or cancer drugs formed by combination of chitosan and radioactive nuclide available now. Some tumor inhibitors or drugs are applied to the affected area through intravenous injections so that the drug requires no clot formation in blood. Moreover, before arriving the affected area, part of drugs is absorbed or interfered by human tissues so that the treatment response and clinical effect are dramatically reduced.

In order to overcome the above shortcomings, the present invention provides a radioactive material containing chitosan for inhibiting cancer and a preparation method thereof that treat cancers or tumors by means of succinimidyl 3,6-diaza-5-oxo-3-[2-((triphenylmethyl)thio)ethyl]-8-[(triphenylmethyl)thio]octanoate (SOCTA) connected with radionuclides and chitosan. Moreover, by features of clotting in alkaline environment of human blood and good biocompatibility of chitosan, the radioactive material containing chitosan is injected directly to the affected area and staying for a long term so as to effectively inhibit cancer cells or tumors. Thus the shortcomings of conventional drugs such as poor treatment response and clinical effect are overcome.

SUMMARY OF THE INVENTION

Therefore it is a primary object of the present invention to provide a radioactive material containing chitosan for inhibiting cancer and a preparation method thereof that use SOCTA compound to connects with radionuclides and chitosan so as to treat cancers or tumors.

It is another object of the present invention to provide a radioactive material containing chitosan for inhibiting cancer and a preparation method thereof that is directly injected into the affected area and stays therein for a long period so as to effectively inhibit or kill cancer cells.

The radioactive material containing chitosan for inhibiting cancer is:

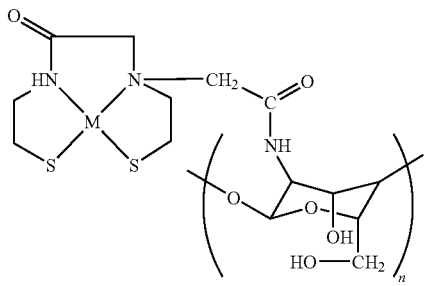

wherein M is selected from nuclides formed by [188]Re and Tc-99m and n ranges from 31 to 8447

A preparation method of radioactive material containing chitosan for inhibiting cancer comprising the steps of: preparing SOCTA-Chitosan compound; and synthesizing M-SOCTA-Chitosan compound. The M is selected from radionuclides formed by [188]Re and Tc-99m.

BRIEF DESCRIPTION OF THE DRAWINGS

The structure and the technical means adopted by the present invention to achieve the above and other objects can be best understood by referring to the following detailed descriptions of the preferred embodiments and the accompanying drawings, wherein.

DETAILED DESCRIPTION OF THE PREFERRED EMBODIMENT

A radioactive material containing chitosan for inhibiting cancer according to the present invention is:

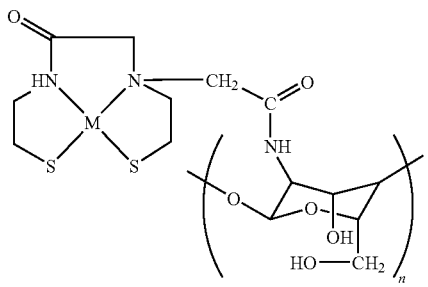

wherein M is selected from radionuclides formed by [188]Re and Tc-99m and n ranges from 31 to 8447 while 188Re is an attractive radioisotope emitting 2.12 MeV β particles that have a maximum penetration in tissue of 10-11 mm, making this radionuclide a suitable option for tumor cells and Tc-99m is also a radioisotope that also kills tumors.

Figure 1:
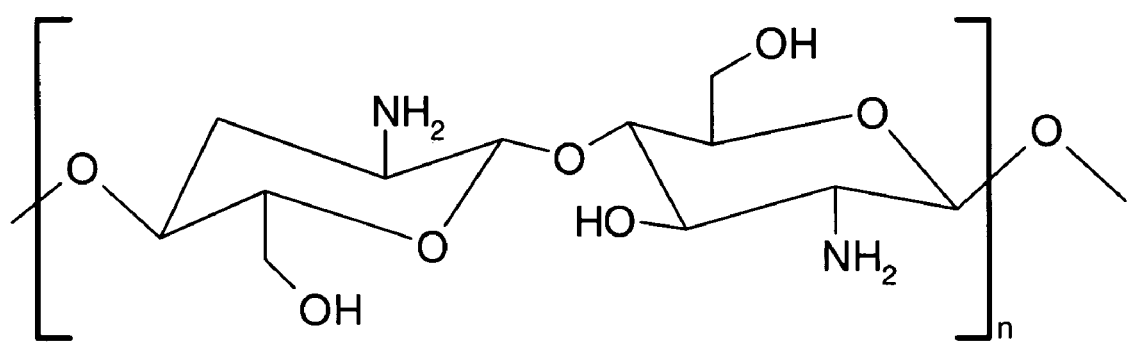
FIG. 1 is chemical formula of chitosan.
Figure 2:
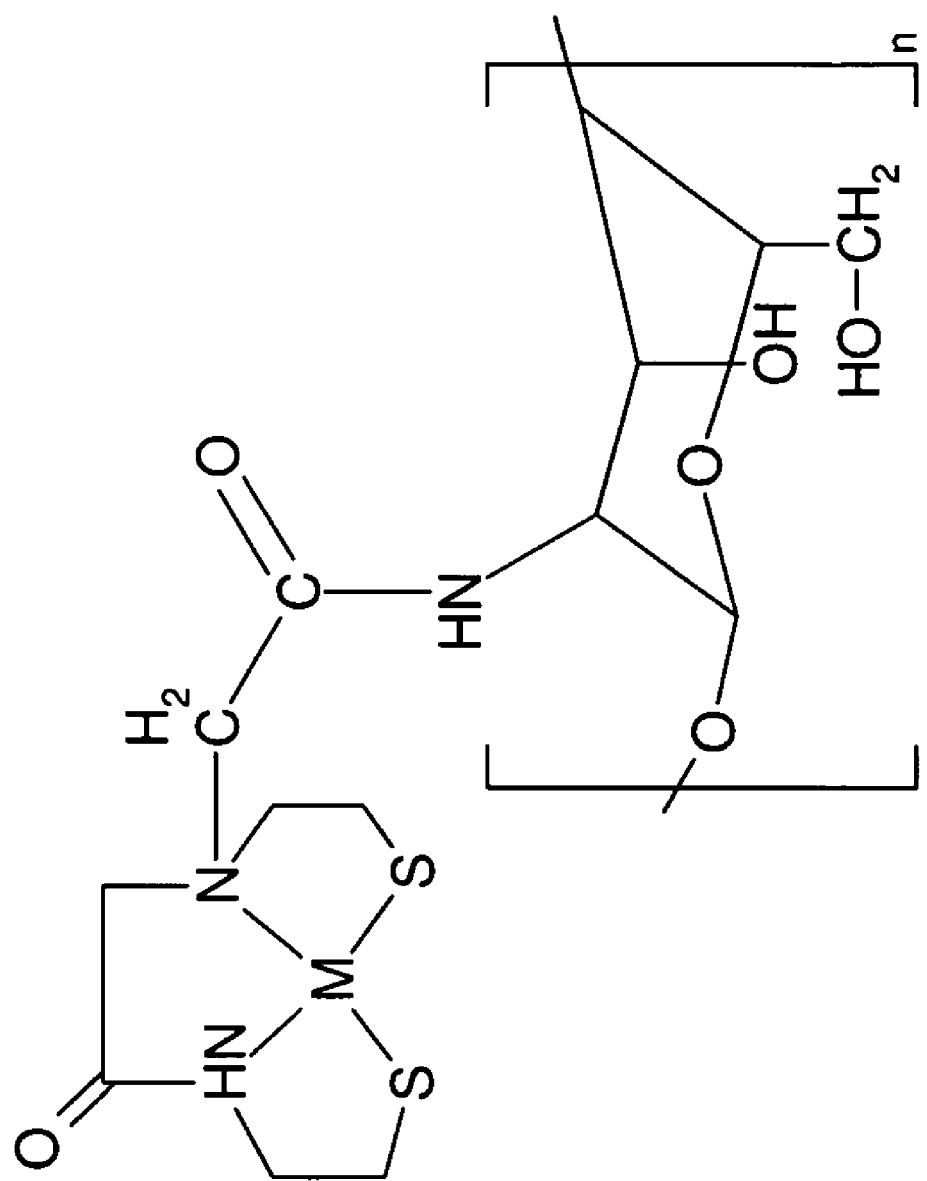
FIG. 2 is a schematic drawing showing chemical formula of radioactive material containing chitosan for inhibiting cancer of an embodiment according to the present invention.
Figure 3:
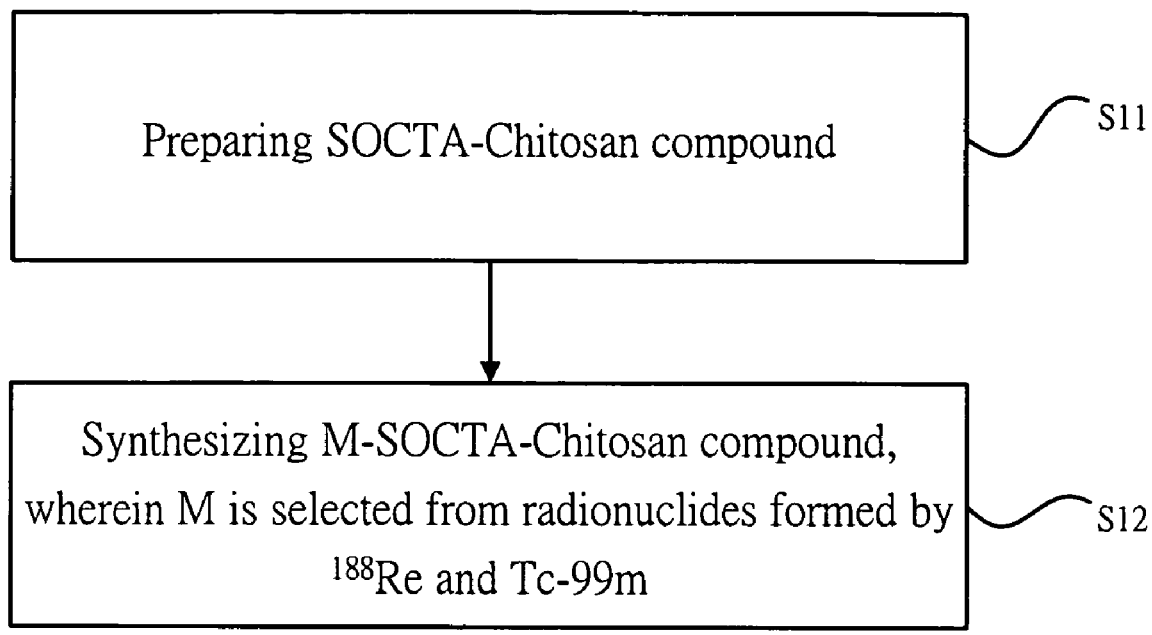
FIG. 3 is a flow chart of a preparation method of radioactive material containing chitosan for inhibiting cancer according to the present invention.
Figure 4:
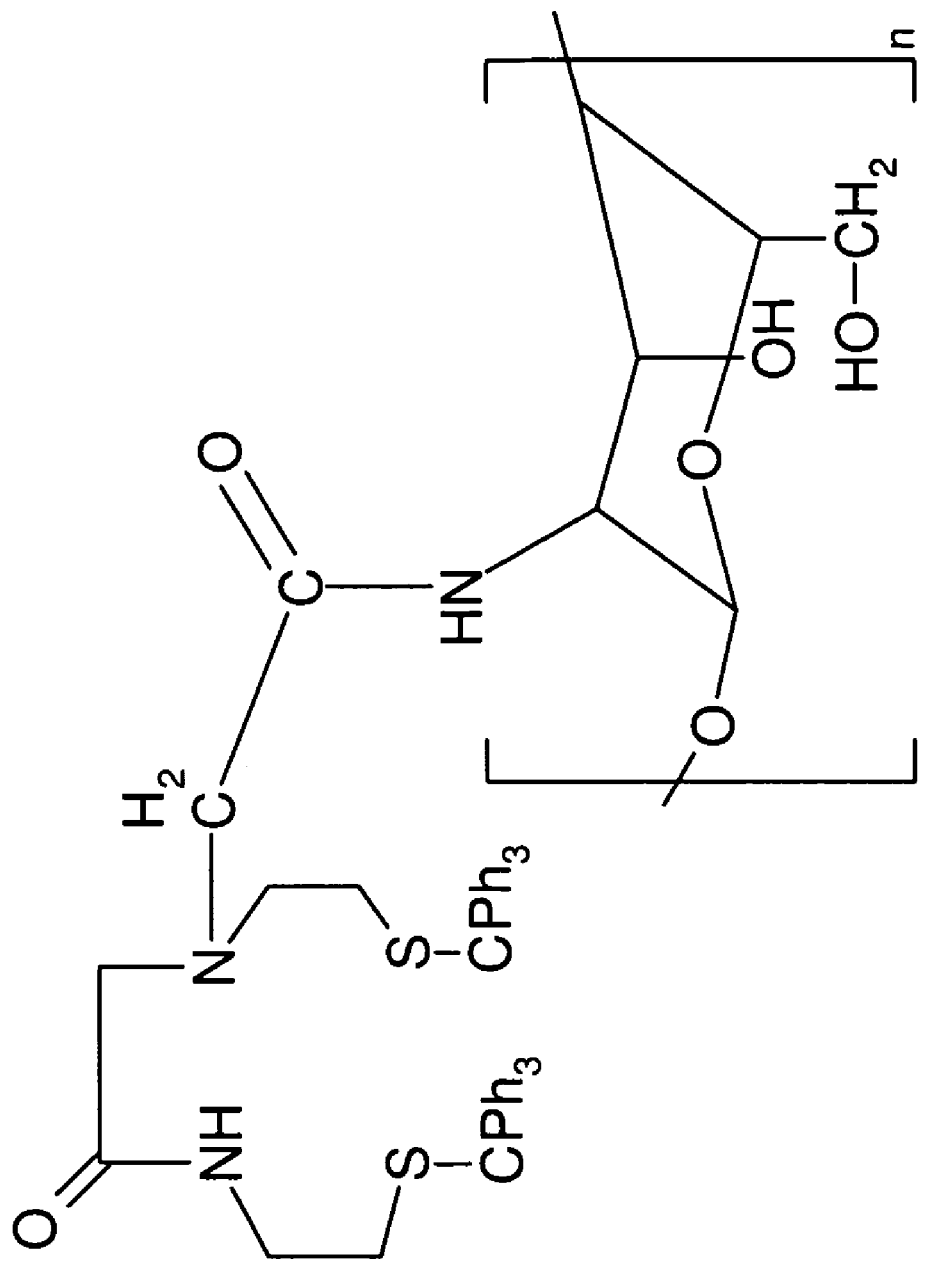
FIG. 4 is a schematic drawing showing chemical formula of SOCTA-Chitosan according to the present invention.

A preparation method of radioactive material containing chitosan for inhibiting cancer includes the following steps, as shown in FIG. 3:

S11 prepare SOCTA-Chitosan compound, the chemical formula is shown in FIG. 4; and S12 synthesize M-SOCTA-Chitosan compound, wherein M is selected from radionuclides formed by [188]Re and Tc-99m.

Figure 5:
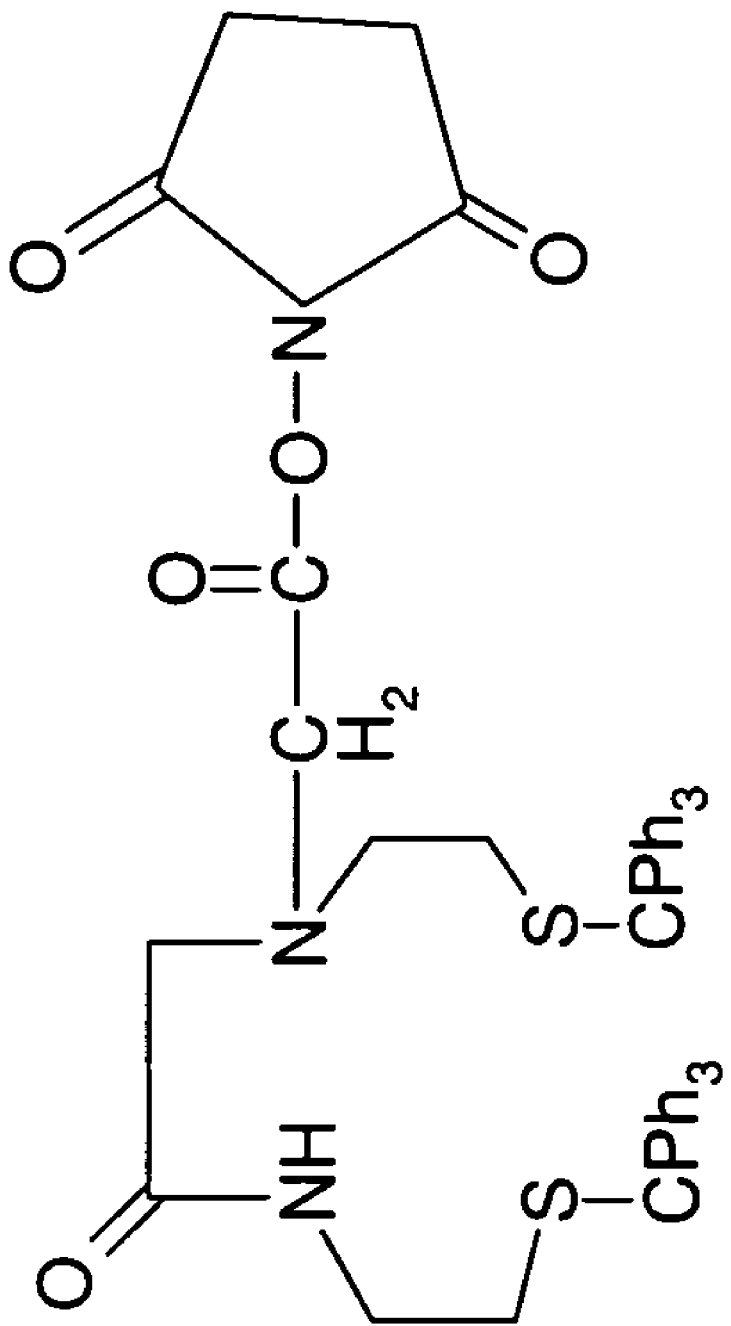
FIG. 5 is a schematic drawing showing chemical formula of SOCTA according to the present invention.
Figure 6D:
FIG. 6D is a microSPECT/CT image 48-hour after the injection of [188]Re-SOCTA-Chitosan into a rat.
Figure 6C:
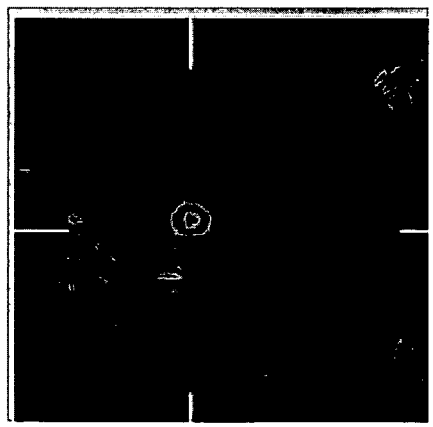
FIG. 6C is a microSPECT/CT image 24-hour after the injection of [188]Re-SOCTA-Chitosan into a rat.
Figure 6B:
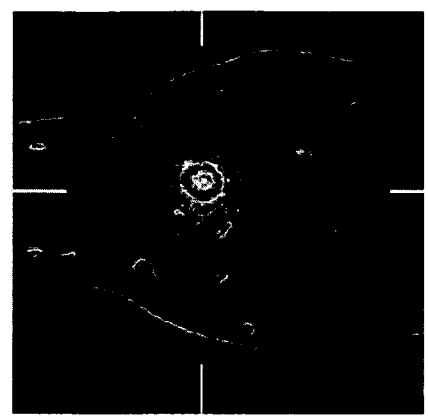
FIG. 6B is a microSPECT/CT image 8-hour after the injection of [188]Re-SOCTA-Chitosan into a rat.
Figure 6A:
FIG. 6A is a microSPECT/CT image 1-hour after the injection of [188]Re-SOCTA-Chitosan into a rat.

Embodiment of a Preparation Method of Radioactive Material Containing Chitosan for Inhibiting Cancer 1. Synthesis of SOCTA-Chitosan Take approximately 2 mg 1-(3-dimethylaminopropyl)-3-ethylcarbodiimide hydrochloride (EDC) and 10 mg Succinimidyl 3,6-diaza-5-oxo-3-[2-((triphenylmethyl)thio)ethyl]-8-[(triphenylmethyl)thio]octanoate (SOCTA) (the chemical formula is shown in FIG. 5) respectively dissolved in 1 ml and 4 ml dimethyl sulfoxide (DMSO) in advance and then mix with each other to form SOCTA solution. Dissolve 30 mg chitosan in 0.1N acetic acid solution completely at room temperature to get chitosan solution. The chitosan solution is slowly titrated into SOCTA solution and is reacted at room temperature for 8 hours. Titrate 0.2 ml 0.1N sodium hydroxide in the reacted solution to form a colloidal suspension of the product, collect the colloid and remove the aqueous solution. Re-suspend the crude colloidal product in a dialysis membrane with PBS (phosphate buffered solution) buffer and dialyze for 48 hours. Next use deionized water and dialyze for another 48 hours. After finishing dialysis, treat the purified colloidal suspension by freeze drying for storage.

Take approximately 0.5 ml [188]Re perrhenate solution, 4 mg stannous chloride ($SnCl_2$), 24 mg glucoheptonate and 4 mg SOCTA-Chitosan, put into a test tube and react at room temperature for 0.5 hour to get labeled [188]Re-SOCTA-Chitosan (the radioactive material containing chitosan for inhibiting cancer). The stannous chloride is reductive, and the glucoheptonate is used as transfer ligand. The SOCTA-Chitosan is labeled at last and the labeling efficiency is over 99% after 30 minutes reaction.

Tumor Cell Culture and Implant

A N1-S1 hepatoma cell line (ATCC, Maryland, USA) is used for tumor implantation. The tumor cells are cultured in Dulbecco's Modified Eagle Medium (GIBCO, Paisley, UK), mixed with 5% fetal bovine serum (FBS), 1% L-glutamine, and 20% horse serum. After one week, the cells are at a density of $4 \times 10^7$ cell/ml. Then assess cell viability by Trypan-blue exclusion test and the cell viability is over 90%. Then implant hepatoma cells into rats for tests.

Use 3 to 4-week old SD-rat (Sprague-Dawley rat), get a 15-2 cm wound with subxiphoid laparotomy and then the rats are anesthetized with Zoletil 50 (50 mg/ml' 0.1 ml/100 g). Inject 0.25 ml N1-S1 cell ($6\times10^6$ cells/ml) into surface layer of the liver. After one week, the rats are ready to be tested.

Medical experiments of [188]Re-SOCTA-Chitosan on animals Take 0.1 mCi/0.1 ml labeled [188]Re-SOCTA-Chitosan, inject into the rat via intratumor injection pathway. Test results of animal models of hepatoma are shown from FIG. 6A to FIG. 6D. Through the microSPECT/CT imaging, it is learned that 48 hours after injection, the [188]Re-SOCTA-Chitosan still stays in tumor cells. This means the present invention do have potential to treat hepatoma. It is believed that by the same injection way, the invention also has potential to treat other kinds of tumors.

In summary, the present invention provides a radioactive material containing chitosan for inhibiting cancer and a preparation method thereof that uses a SOCTA compound connected with radionuclides and chitosan to treat cancer. Moreover, according to the features of clotting in alkaline environment of human blood and good biocompatibility of chitosan, the radioactive material containing chitosan is injected directly to the affected area and staying for a long term so as to effectively inhibit cancer cells or tumors.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A radioactive material containing chitosan for hepatoma cancer treatment, comprising:

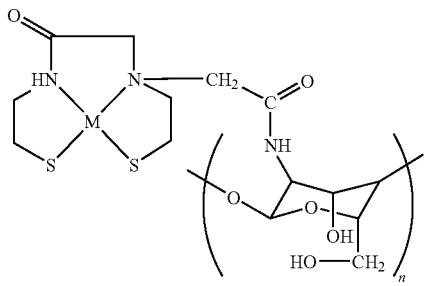

wherein M is selected from the group of radionuclides consisting of [188]Re and Tc-99m, and n ranges from 31 to 8447.

2. A method of preparing the radioactive material as claimed in claimed 1, comprising the steps of:
 (i) preparing a SOCTA-Chitosan compound, wherein the step comprises:
  a) dissolving 1-(3-dimethylaminopropyl)-3-ethylcarbdiimidehydrochloride (EDC) and succinimidyl 3,6-diaza-5-oxo-3-[2-((triphenylmethyl)thio)ethyl]-8-[(triphenylmethyl)thio]octanoate (SOCTA) into dimethyl sulfoxide (DMSO) separately and then mixing them together to form a SOCTA solution;
  b) dissolving chitosan in acetic acid at room temperature to form a chitosan solution; and
  c) adding the chitosan solution into the SOCTA solution slowly at room temperature, to form a reacted solution which is the solution of the SOCTA-Chitosan compound; and
 (ii) synthesizing a 188Re-SOCTA-Chitosan compound or a Tc-99m-SOCTA-Chitosan compound, wherein the step comprises:
  mixing 188Re perrhenate solution, stannous chloride, glucoheptonate, and the SOCTA-Chitosan compound together, to form the 188Re-SOCTA-Chitosan compound, or
  mixing Tc-99m perrhenate solution, stannous chloride, glucoheptonate, and the SOCTA-Chitosan compound together, to form the Tc-99m-SOCTA-Chitosan compound.

3. The method as claimed in claim 2, further comprising a step of adding sodium hydroxide to the reaction mixture after completion of the reaction step to generate a colloidal suspension of the SOCTA-chitosan compound.

4. The method as claimed in claim 3, further comprising a first dialysis step with PBS buffer for 48 hours, followed by a second dialysis step with deionized water for 48 hours.

5. A radioactive material, comprising:

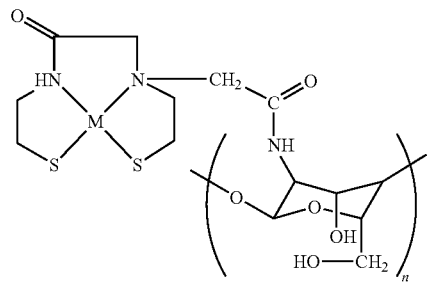

wherein M is selected from the group of radionuclides consisting of 188Re and 99mTc, and n ranges from 31 to 8447.

* * * * *